US009896491B2

(12) United States Patent
Belogurov et al.

(10) Patent No.: US 9,896,491 B2
(45) Date of Patent: Feb. 20, 2018

(54) COMPOSITION FOR TREATMENT OF MULTIPLE SCLEROSIS

(75) Inventors: Aleksey Anatolievich Belogurov, Moscow (RU); Alexandr Gabibovich Gabibov, Moscow (RU); Natalya Alexandrovna Ponomarenko, Moscow (RU)

(73) Assignee: LIFEBIO LABORATORIES LLC, Wyoming, DE (US)

( * ) Notice: Subject to any disclaimer, the term of this patent is extended or adjusted under 35 U.S.C. 154(b) by 119 days.

(21) Appl. No.: 13/443,981

(22) Filed: Apr. 11, 2012

(65) Prior Publication Data

US 2012/0207820 A1    Aug. 16, 2012

Related U.S. Application Data

(63) Continuation-in-part of application No. PCT/RU2009/000533, filed on Oct. 12, 2009.

(51) Int. Cl.

| A61K 38/10 | (2006.01) |
| A61P 25/00 | (2006.01) |
| A61K 9/127 | (2006.01) |
| C07K 4/12 | (2006.01) |
| C07K 7/08 | (2006.01) |
| A61K 38/17 | (2006.01) |
| C07K 14/47 | (2006.01) |
| A61K 39/00 | (2006.01) |

(52) U.S. Cl.
CPC ...... *C07K 14/4713* (2013.01); *A61K 39/0005* (2013.01)

(58) Field of Classification Search
None
See application file for complete search history.

(56) References Cited

U.S. PATENT DOCUMENTS 5,858,980 A * 1/1999 Weiner .................. A61K 38/39
                                                        514/17.7
2005/0209156 A1    9/2005 Warren
2008/0200368 A1    8/2008 Wraith

FOREIGN PATENT DOCUMENTS

| EP | 1918298 A2 | 5/2008 |
| WO | 9308212 A1 | 4/1993 |
| WO | 1996/012737 A2 | 5/1996 |
| WO | 1998/045327 A1 | 10/1998 |
| WO | 2003/064464 A1 | 8/2003 |
| WO | 2009/056833 | 10/2008 |
| WO | 2008151847 A1 | 12/2008 |
| WO | 2009047009 A1 | 4/2009 |
| WO | 2009056833 A2 | 5/2009 |

OTHER PUBLICATIONS

Crommelin et al. (Journal of Controlled Release, 46 (1997) 165-175).*
GenScript (FAQ: custom peptide synthesis, Mar. 22, 2009).*
Torchilin ("Recent Advances with Liposomes as Pharmaceutical Carriers", Nature Reviews/Drug Discovery, vol. 4, Feb. 2005, pp. 145-160).*
D. Hafler, Multiple sclerosis, The Journal of Clinical Investigation 113(6): 788-794. (2004).
Kornek, et al., Neuropathology of multiple sclerosis-new concepts, Brain Research Bulletin 61: 321-326. (2003).
Merkler, et al., "Viral deja vu" elicits organ-specific immune disease independent of reactivity to self, The Journal of Clinical Investigation 16(5): 1254-1263. (2006).
Hohlfeld, et al., Autoimmune concepts of multiple sclerosis as a basis for selective immunotherapy: From pipe dreams to (therapeutic) pipelines, PNAS 101, suppl. 2: 14599-14606. (2004).
Allegreta, et al., T Cells Responsive to Myelin Basic Protein in Patients with Multiple Sclerosis, Science 247: 718-721. (1989).
Richert, et al., Evidence for multiple human T cell recognition sites on myelin basic protein, Journal of Neuroimmunology 23: 55-66. (1989).
Altmann, et al., Activation of specific T cell lines by the antigens avidin and myelin basic protein in the absence of antigen-presenting cells, Eur. J. Immunol. 17: 1635-1640. (1987).
Klawiter, et al., B Cells: No Longer the Nondominant Arm of Multiple Sclerosis, Current Neurology and Neuroscience Reports 7: 231-238. (2007).
Nikbin, et al., Role of B Cells in Pathogenesis of Multiple Sclerosis, International Review of Neurobiology 79: 13-42. (2007).
Reindl, et al., Antibodies against the myelin oligodendrocyte glycoprotein and the myelin basic protein in multiple sclerosis and other neurological diseases: a comparative study, Brain 122: 2047-2056. (1999).
Genain, et al., Identification of autoantibodies associated with myelin damage in multiple sclerosis, Nature Medicine 5(2): 170-175. (1999).
Berger, et al., Antimyelin Antibodies as a Predictor of Clinically Definite Multiple Sclerosis after a First Demyelinating Event, N ENGL J MED 349: 139-145. (2003).
Warren, et al., Diagnostic Value of Cerebrospinal Fluid Anti-Myelin Basic Protein in Patients with Multiple Sclerosis, Ann Neurol 20: 20-25. (1986).
Stüve, et al., Long-term B-Lymphocyte Depletion With Rituximab in Patients With Relapsing-Remitting Multiple Sclerosis, Arch Neurol. 66(2): 259-261. (2009).

(Continued)

*Primary Examiner* — James H Alstrum-Acevedo
*Assistant Examiner* — Tara L Martinez
(74) *Attorney, Agent, or Firm* — Troutman Sanders LLP

(57) ABSTRACT

Novel oligopeptides, combinations thereof and fusion proteins composed of the above-mentioned oligopeptides are disclosed. Oligopeptides are homologous in amino acid sequence to the selected parts of the amino acid sequence of human myelin basic protein (MBP) and are capable to ameliorate the progression of multiple sclerosis by means of binding to and inactivation of epitope-specific anti MBP catalytic auto antibodies (ESAMBPCAA) involved into binding and catalytic degradation of MBP in course of progression of Multiple Sclerosis.

9 Claims, 4 Drawing Sheets

(56) References Cited

OTHER PUBLICATIONS

Goodkin, et al., A phase I trial of solubilized DR2:MBP84-102 (AG284) in multiple sclerosis, Neurology 54: 1415-1420. (2000).
Ponomarenko, et al., Catalytic activity of autoantibodies toward myelin basic protein correlates with the scores on the multiple sclerosis expanded disability status scale, Immunology Letters 103: 45-50. (2006).
Belogurov, et al., Suppression of ongoing experimental allergic encephalomyelitis in DA rats by novel peptide drug, structural part of human myelin basic protein 46-62, Autoimmunity 42(4): 362-364. (2009).
Belogurov, et al., Recognition and Degradation of Myelin Basic Protein Peptides by Serum Autoantibodies: Novel Biomarker for Multiple Sclerosis, J Immunol 180: 1258-1267. (2008).
Valli, et al., Binding of Myelin Basic Protein Peptides to Human Histocompatibility Leukocyte Antigen Class II Molecules and Their Recognition by T Cells from Multiple Sclerosis Patients, J. Clin. Invest. 91: 616-628. (1993).
Fritz, et al., Induction of experimental allergic encephalomyelitis in PL/J and (SJL/J x PL/J)F1 mice by myelin basic protein and its peptides: localization of a second encephalitogenic determinant, J Immunol 131(1): 191-194. (1983).
Kamholz, et al., Identification of three forms of human myelin basic protein by cDNA cloning, PNAS 83: 4962-4966. (1986).
G. A. Hashim, Failure of Myelin Basic Protein to Prevent or Suppress Experimental Allergic Encephalomyelitis in Guinea Pigs, Neurochemical Research 5(2): 101-113. (1980).
Catz, et al., Intrathecal Synthesis of Autoantibodies to Myelin Basic Protein in Multiple Sclerosis, Can. J. Neural. Sci. 13:21-24, (1986).
Stromnes, et al., Active induction of experimental allergic encephalomyelitis, Nature Protocols 1(4): 1810-1819. (2006).
International Search Report and Written Opinion Issued in PCT/RU2009/000533 dated Sep. 21, 2010, 10 pages.
International Preliminary Report on Patentability Issued in PCT/RU2009/000533 dated Feb. 6, 2012, 32 pages.
Schwartz, Robert S., "Autoimmunity and Autoimmune Diseases", Fundamental Immunology, Third Edition (1993), Paul W. E. (Raven Press, New York), pp. 1033-1097.
Poser et al. "Diagnostic criteria for multiple sclerosis", Clin. Neurol. Neurosurg (2001) vol. 103, p. 1-11.
Miller et al., "Experimental autoimmune encephalomyelitis in the mouse", Animal Models for Autoimmune and Inflammatory Disease Unit 15.1.1 (2010), In: Current Protocols in Immunology; J. E. Coligan, ed. Wiley, New York, p. S19.
Warren, K.G. et al, European Journal of Immunology, 2006, vol. 13, No. 8, pp. 887-895.
Johnson KP, Brooks BR, Cohen JA, Ford CC, Goldstein J, Lisak PP et al. Copolymer-1 reduces relapse rate and improves disability in relapsing-remitting multiple sclerosis: Results of a phase III multicentre, double-blind, placebo controlled trial. The copolymer-1 multiple sclerosis study group. Neurology 1995; 45:1268.
Paty DW, Li DKB, the UBC MS/MRI Study Group and the Interferon Beta Multiple Sclerosis Study Group. Interferon beta-lb is effective in relapsing-remitting multiple sclerosis. II. MRI results of a multi-centred, double-blind, placebo-controlled trial. Neurology 1993;43:662-7.

\* cited by examiner

Primary structure (amino acid sequence) of human MBP (SEQ ID NO: 1)

1   ASQKRPSQRH GSKYLATAST MDHARHGFLP RHRDTGILDS IGRFF GGDRG
    APKRGSGKDS 60
61  HH PARTAHYG SLPQKSHGRT QDENPVVHFF KNIVTPRTPP PSQGKGRGLS
    LSRFSWGAEG 120
121 QRP GFGYGGR ASDYKSAHK G FKGVDA QGTL SKIFKLGGRD SRSGSPMARR   170

SEQUENCE ID 2:
GGDRGAPKRGSGKDSHH

SEQUENCE ID 3:
GFGYGGRASDYKSAHK

SEQUENCE ID 4:
QGTLSKIFKLGGRDSRSGSPMARR

Fig. 1

COMPOSITION FOR TREATMENT OF MULTIPLE SCLEROSIS

CROSS-REFERENCE TO RELATED APPLICATION

This application is a continuation-in-part of International Application No. PCT/RU2009/000533, filed on Oct. 12, 2009, which published as WO 2011/046462 on Apr. 21, 2011, and which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 6, 2015, is named 245032.000003_SL.txt and is 9,674 bytes in size.

FIELD OF INVENTION

The present invention relates to oligopeptides and fusion proteins and their use in the inactivation of epitope-specific anti MBP catalytic auto antibodies (ESAMBPCAA) involved into binding and catalytic degradation of MBP in course of progression of Multiple Sclerosis. The invention also relates to pharmaceutical compositions comprising said oligopeptides, combinations of the said oligopeptides and fusion proteins composed of the above-mentioned oligopeptides and their use for the treatment of multiple sclerosis.

BACKGROUND ART

Multiple sclerosis (hereinafter abbreviated as MS) is an inflammatory demyelinating disease of the human central nervous system with heterogeneous pathophysiological and clinical manifestations and a very complicated etiology (Hafler et al., 2004. J. Clin. Invest. 113: 788-794; Kornek et al., 2003. Brain Res. Bull. 61: 321-326). Progression of the disease in humans leads to destruction of the myelin sheath and that ultimately affects the ability of nerves to conduct electrical impulses (Schwartz, R. S., 1993, in Fundamental Immunology, ed. Paul, W. E. (Raven, New York), pp. 1033-1097).

The viral mimicry hypothesis was formulated to explain the initiation of this pathology (Merkler et al., 2006. J. Clin. Invest. 116: 1254-1263). At present, however, the true triggering mechanisms of the disease have not been clearly identified (Hohlfeld et al., 2004. Proc. Natl. Acad. Sci. USA 101 (Suppl. 2): 14599-14606).

It has been demonstrated that some of the proliferating T-cells in MS patients are directed towards MBP (Allegretta et al., Science, 247, 718-721, 1990) and that human T-cells can recognize multiple epitopes on the MBP molecule (Richert et al., J. Neuroimmun 23, 55-66, 1989). MBP also appears to be capable of activating some T-cells without the involvement of antigen presenting cells (Altman et al., Eur. J. Immun. 17, 1635-1640, 1987).

Despite strong and commonly accepted evidence for immune T cell involvement in development and progression of MS in humans and experimental animal models of the disease, the contributions of a specific B cell response to myelin sheath destruction is much less investigated (Klawiter et al., 2007. Curr. Neurol. Neurosci. Rep. 7: 231-238; Nikbin et al., 2007. Int. Rev. Neurobiol. 79: 13-42).

Ample data indicate that a significant portion of MS cases is characterized by the presence in the blood of auto antibodies directed against MBP components (Reindl et al., 1999, Brain, 122, 2047-2056; Genain et al., 1999, Nat. Med. 5, 170-175). Moreover, high resolution microscopic analysis detected myelin-specific auto antibodies in the regions of demyelination plaques in human MS and a MS-like disease of marmosets, suggesting their direct contribution to myelin destruction (Genain et al., 1999, Nat. Med. 5, 170-175). Although the mechanism of the autoantibody role in MS pathogenesis is unknown, auto antibodies to MBP and myelin oligodendrocyte glycoprotein (MOG) were proposed as biomarkers for clinical prognosis of MS (Berger et al., 2003, N. Engl. J. Med. 349, 139-145.10). Similar immunoglobulins were also found in mice with induced experimental allergic encephalomyelitis (EAE), which is an animal model of MS (Fritz et al., 1983, J. Immunol. 130, 191-194). Increased titers of auto antibodies to MBP were observed in the cerebrospinal fluid (CSF) of patients with active forms of MS (Warren at al., Ann Neurol 209:20-25, 1986). Clinically, MS is characterized by phases of disease activity such as acute relapses or chronic progression, and by phases of clinical remission. Active MS is associated with increased levels of intrathecally appearing auto antibodies to MBP (Warren et al., Ann Neurol 209:20-25, 1986; Catz et al., Can J Neurol Sci 13:21-24, 1986). These antibodies are found predominantly in free (F) form during acute relapses and predominantly in bound (B) form when the disease is insidiously progressive (Warren et al., Ann Neurol 209:20-25, 1986). The therapy of relapsing-remitting multiple sclerosis (RRMS) patients with rituximab a monoclonal antibody, which selectively targets and depletes CD20+ B lymphocytes, appears safe and effective to some extend (Stüve, O. et al., Long-term B-lymphocyte depletion with rituximab in patients with relapsing-remitting multiple sclerosis, Arch Neurol. 2009 February; 66(2):259-61).

Accordingly to that existing scientific background, the approach to treat MS using the immunomodulation with the whole MBP molecule and numerous peptides representing fragments and homologs of MBP protein and its fragments has been developed during last decade. As it is well known human MBP consists of 170 amino acid residues. In scientific and patent literature a fragment of MBP is labeled according to positions of its first and last amino acid residues counted from the C-terminus of full MBP sequence (SEQ ID NO: 1).

In WO 9612737 a number of peptides (human MBP fragments) having "T-cell activity" (i.e. the ability to influence on activity or functions of immune T-cells or their subpopulations) were provided for preventing and treating of MS and has been disclosed as suitable for therapeutic use. To reveal the T-cell recognized epitopes in MBP, 16 short (each about 20 amino acid residues in length) and three more long (82-100, 83-105, 141-165) "overlapping" each other peptide sequences have been tested on their ability to stimulate of in vitro proliferation of peripheral blood cells of MS patients. The amino acid structure of peptides provided by inventors corresponds to the following MBP fragments: 11-30; 11-29; 11-31; 83-105; 82-105; 82-104; 80-98; 82-102; 80-104; 80-102; 111-130; 111-129; 141-165; 101-125. Also, these authors disclosure combination of the inventive peptides with others peptides known from prior art as having T-cell activity of MBP: 13-25; 31-50; 61-80; 82-92; 82-96; 82-97; 82-98; 82-100; 83-100; 83-101; 84-97; 84-100; 85-100; 86-105; 87-99; 87-99 [91K>A]; 88-100; 88-99; 82-100; 111-135; 122-140; 139-170; 141-160; 142-166; 142-168; 146-160; 153-170.

Wraith D. C. and co-authors provide a method for selecting of tolerogenic peptides capable of binding to an MHC class I or II molecules without further antigen processing and using these peptides in a pharmaceutical composition for treatment and/or prevention of multiple sclerosis. A number of peptides corresponded to fragments 1-24; 15-39; 30-54; 45-69; 60-84; 75-99; 90-114; 105-129; 120-144; 135-159; 150-170; 131-145; 132-146; 133-147; 134-148; 135-149; 136-150; 137-151; 138-152; 139-153; 140-154; 141-155; 142-156; 143-157; 144-158 of human MBP have been synthesized and used by these authors for identification of human MBP epitopes recognized by MS-patients' peripheral blood cells and then for study of ability of these peptides to bind to MHC class I or class II molecules. A number of short peptides, active in respect of modulation of immune T-cell functions were selected and claimed for MS treatment: 134-148; 135-149; 136-150; 137-151; 138-152; 139-153; 140-154; 30-44; 80-94; 83-99; 81-95; 82-96; 83-97; 84-98; 110-124; 130-144; 131-145; 132-146; 133-147 (see Applications: EP1918298, U.S. Ser. No. 11/979,224, WO 03/64464).

In US2005209156 a peptide selected from MBP fragment (75-98) having the amino acid sequence of AGAPVVHPPLAIVTPAT (SEQ ID NO: 5) including substitutions, additions or deletions thereof, has been disclosed for MS treatment.

In U.S. Pat. No. 5,858,980 the MBP fragments 84-102 and 143-168 were identified as containing immunodominant T-cell recognized epitopes of MBP active in the development of MS, and peptide comprising the amino acid sequence of ENPVVHFFKNIVTPRT (SEQ ID NO: 6) (MBP fragment 83-98) and their analogs and AQGTLSKIFKLGGRD (SEQ ID NO: 7) (MBP fragment 146-160) as well as a pharmaceutical composition comprising the peptides were provided.

Warren K. G. with coauthors provides soluble synthetic peptides, useful to neutralize anti MBP auto antibodies, having the amino acid sequence correspond to following amino acid residues of human MBP: 61-75; 64-78; 69-83; 75-95; 69-83; 80-97; 91-106; 84-93; 85-94; 86-95; 87-96; 82-98. These peptides overlap MBP sequence from 61 to 106 of its amino acid residues (see WO 98/45327). One of the selected peptides (namely MBP 75-95) showed its ability to bound free antibodies to MBP both in vitro and in vivo (in blood of MS-patients). On the contrary, non-binding, control peptide MBP 35-58 had no effect on free and bound antibodies to MBP in MS patients.

Some of MBP based peptides and DNA vaccines has been evaluated in clinical trials: Bayhill Therapeutics DNA-vaccine BHT-3009 containing the gene for whole MBP sequence; altered peptide ligands GP77116 and NBI-5788 from Neurocrine Biosciences; oral tolerogenic composition Myloral from Autoimmune(R) based on whole MBP sequence. However no significant success was observed from those therapies due to serious adverse events or inability to slow MS progression (Hohlfeld et al., Proc Nat Acad. Sci USA. 2004, Oct. 5; 101 (Suppl. 2): 14599-14606.). Now the abovementioned synthetic peptide with a sequence corresponding to amino acid residues 82-98 of MBP (DENPVVHFFKNIVTPRT (SEQ ID NO: 8)) and coded as MBP8298 is being extensively studied in phase II of clinical trials for treatment of progressive multiple sclerosis. The peptide at dose of 500 mg was administered intravenously every six months. It has been shown that responders on the treatment with MBP8298 are the patients with HLA heliotypes DR2 and/or DR4 only (Warren, K. G. et al. European Journal of Immunology, 2006, vol. 13, No 8, pp. 887-895).

Above-mentioned MBP 84-102 fragment (U.S. Pat. No. 5,858,980) was used as active ingredient for preparation for treatment of secondary progressive MS in phase I of clinical trials. No treatment efficacy were detected according to measurement of Expanded Disability Status Scale, Nine Hole Peg Test, new lesions diagnosed by Magnetic Resonance Imaging (Goodkin, D. E. et al. Neurology 2000, vol. 54, pp. 1414-1420)

Thus the search and selection of novel fragments of MBP, oligopeptides having therapeutic activity against MS represents non-trivial task and medicinal properties of any of such oligopeptides with respect to MS treatment cannot be predicted beforehand by a person skilled in the art even on the basis of extensive preclinical in vitro and/or in vivo testing. The identification and selection of such new effective peptides may be achieved through discovery of novel immunopathological mechanisms involved into development and progression of MS.

Earlier we have presented evidence that a small fraction of anti-MBP auto antibodies circulating in blood of MS patients demonstrates site-specific proteolytic cleavage of the MBP molecule and represents novel immunopathological mechanism of myelin destruction and progression of MS (Ponomarenko et al. Immunology Letters 103, 2006, pp. 45-50)

Accordingly, the object of the present invention is to determine novel oligopeptides which would be able to neutralize epitope-specific anti MBP auto antibodies involved into binding and catalytic degradation of MBP in course of progression of Multiple Sclerosis (ESAMBPCAA-epitope specific anti MBP catalytic auto antibodies), and new effective methods of treating MS using these novel oligopeptides.

This object is achieved by providing novel oligopeptide moieties (oligopeptides, fusion proteins composed of these oligopeptides and fragments of these oligopeptides), a pharmaceutical composition containing the said oligopeptides and fusion proteins, which neutralize ESAMBPCAA. Surprisingly, despite ESAMBPCAA represent only minor fraction of circulating anti MBP auto antibodies in MS, the inventors of the present invention have discovered that oligopeptides having sequences comprising as short as 6 amino acid residues of SEQ ID NO: 2, which neutralize ESAMBPCAA, demonstrate unexpectedly high efficacy in treatment of MS.

Other advantages and aspects of the present invention will become apparent upon reading the following detailed description of the invention.

BRIEF SUMMARY OF THE INVENTION

In one embodiment, the present invention provides an oligopeptide (I) having amino acid sequence GGDRGAPKRGSGKDSHH (SEQ ID NO: 2).

In a further embodiment, the present invention provides an oligopeptide comprising one or more amino acid sequence alterations in SEQ ID NO: 2, wherein said oligopeptide contains at least 6 contiguous amino acid residues of SEQ ID NO: 2 and is capable of binding ESAMBPCAA.

In still further embodiment, the present invention provides a fragment of oligopeptide I or a fragment of oligopeptide I comprising one or more amino acid sequence alterations in SEQ ID NO: 2, wherein said fragment has at least 6 amino acid residues in length and is capable of binding ESAMBPCAA.

In a further embodiment, the present invention provides a pharmaceutical composition comprising as an active ingredient a therapeutically effective amount of any one of the following oligopeptides:

an oligopeptide I having amino acid sequence GGDR-GAPKRGSGKDSHH (SEQ ID NO: 2);

an oligopeptide comprising one or more amino acid sequence alterations in SEQ ID NO: 2, wherein said oligopeptide contains at least 6 contiguous amino acid residues of SEQ ID NO: 2 and is capable of binding ESAMBPCAA;

a fragment of the oligopeptide I having amino acid SEQ ID NO: 2 or a fragment of an oligopeptide comprising one or more amino acid sequence alterations in SEQ ID NO: 2, wherein said fragment has at least 6 amino acid residues in length and is capable of binding ESAMB-PCAA, and a pharmaceutically acceptable carrier or diluent or drug delivery system.

In another embodiment, the present invention provides a pharmaceutical composition comprising as an active ingredient, a therapeutically effective amount of oligopeptide I having amino acid sequence SEQ ID NO: 2 or a fragment thereof, or an oligopeptide comprising one or more amino acid sequence alterations in SEQ ID NO: 2, or a fragment thereof, as set forth above and further comprising at least one oligopeptide selected from oligopeptide II having sequence SEQ ID NO: 3 and oligopeptide III having SEQ ID NO: 4.

In another embodiment, the present invention provides a fusion peptide composed of two or more peptides that are different or identical and are selected from the group of oligopeptides having sequence SEQ ID NO: 2, SEQ ID NO: 3, and SEQ ID NO: 4 or fragments thereof, which are linked sequentially to each other via a peptide or non-peptide linker in any order, wherein the fusion protein comprises at least one oligopeptide of SEQ ID NO: 2 or a fragment thereof.

In a preferred embodiment, a fusion peptide according to the present invention is composed of fragments of a sequence ID SEQ NO: 2, the fragments having at least 6 amino acid residues in length and linked sequentially to each other via a peptide or non-peptide linker.

In a further embodiment of the invention, a method for treating multiple sclerosis is provided, the method comprising administering an effective dose of an oligopeptide, or a fragment thereof, or a fusion peptide, or a pharmaceutical composition of the present invention to a subject in need thereof.

In a particular embodiment of the invention, the method for treating multiple sclerosis comprises: exposing the blood of a patient suffering from multiple sclerosis to an effective dose of an oligopeptide, or a fragment, or a fusion peptide or a pharmaceutical composition according to the present invention.

In another embodiment, use of an oligopeptide or a fusion protein of the present invention for manufacturing of a medicament for treating multiple sclerosis is provided.

BRIEF DESCRIPTION OF THE DRAWINGS

FIG. 1 shows the amino acid sequence of intact human-MBP molecule. The block capitals represent amino acid residues on human MBP. Also the parts of MBP-amino acid sequence which correspond to amino acid sequence of inventive oligopeptide (SEQ ID NO: 2) as well as of oligopeptides having amino acid sequence SEQ ID NO: 3 and SEQ ID NO: 4, are presented correspondingly. These parts of MBP-amino acid sequence are outlined with black line.

DETAILED DESCRIPTION OF THE INVENTION

Definitions

Figure 2:
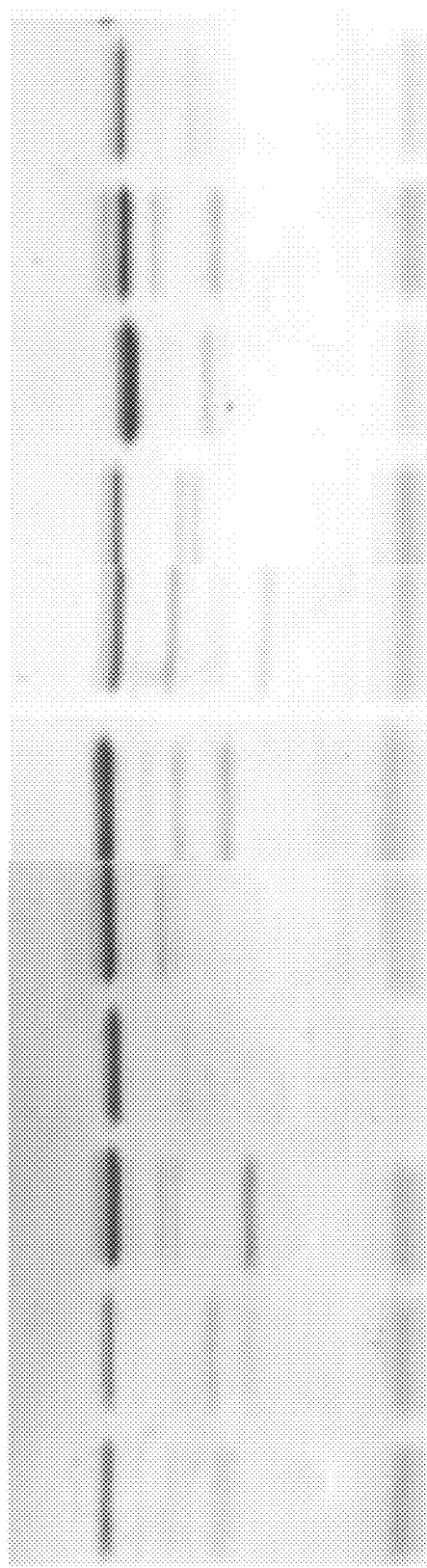
FIG. 2 shows degradation of MBP in presence of ESA-MBPCAA and inhibition of degradation in presence of different MBP peptide fragments (the horizontal row of figures correspond to positions of first and last amino acid residues counted from the C-terminus of full MBP sequence).

As used herein, the term "oligopeptide" relates to any molecule that contains up to about 20 amino acid residues linked by peptide linkage(s), i.e. term "oligopeptide" means a polypeptide up to 20 amino acids in length. The term "oligopeptide" or "oligopeptides" encompasses oligopeptides as well as salts thereof. Suitable salts include sodium or potassium salts or acetic or phosphate salts.

As used in this description, the term "oligopeptide" encompasses an "oligopeptide" having specified amino acid sequence and functional variants thereof. The functional variants include any fragment of the oligopeptide of specified sequence wherein the fragment has from 6 to 20 amino acids in length provided that is retains capability of binding ESAMBPCAA.

As used in this description, the term an oligopeptide "fragment" of the present invention is comprised of at least about 6, preferably at least about 8, preferably at least about 12, more preferably at least about 14, and most preferably at least about 16 or more contiguous amino acid residues.

Further contemplated are variants of the oligopeptides of present invention obtained by altering the amino acid sequence of parent oligopeptide. Such alterations can comprise one or more amino acid substitutions, deletions, insertions or additions provided that resulting variant comprised at least 6 contiguous amino acids of the parent sequence and is capable of binding ESAMBPCAA.

As used in this description, the tam "fusion peptide" or "fusion protein" refers to an oligopeptide or a fragment thereof fused to another oligopeptide or a fragment thereof, each fused moiety being bound to the other directly by a peptide link (the amino group ($NH_2$) of N terminus of one oligopeptide linked to the carboxylic acid group (COOH) of C-terminus of the other oligopeptide or a fragment thereof) or alternatively via a linker. The "linker" may be selected from "peptide linker" or "non-peptide linker". A "peptide linker" may consist of a sequence containing from about 1 to about 20 amino acids, which are linearly linked to each other by peptide bond and which may optionally include a sequence for a protease cleavage site. The term "non-peptide linker" as used herein refers to any linking moiety having two or more reactive groups other than peptide linker. Preferred linker is a non-peptide polymer. The non-peptide polymer used a linker of the invention is a polymer carrying reactive groups at both ends, which are capable of independently binding to reactive groups of an oligopeptide, wherein examples of reactive group of the oligopeptide includes a terminal amino group or a terminal carboxyl group, a lysine residue, a histidine residue or a cysteine residue. Reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at the ends of a non-peptide polymer may be the same or different. For example, the polymer may have a maleimide group at one end and an aldehyde group at another end. Low molecular weight linkers include carbodiimide or glutaraldehyde.

As used in this description, the term "ESAMBPCAA" refers to small fraction of autologous immunoglobulin molecules circulating in blood of MS patient which binds myelin basic protein and catalyze site-specific proteolytic cleavage of the MBP molecule.

As used in this description the terms "to treat," "treating," and "treatment" refer to administering a therapy, an agent, a compound, or composition to a subject suffering from a disease in order to reduce, ameliorate or to eliminate at least one symptom of the condition being treated as assessed by attending physician or any skilled in the art by any conventional method. As used in this description, the term 'Neutralization, inactivation, inhibition' means reduction of specific activity as measured with specified appropriate test system.

As used in the description, "effective amount" is an amount of an oligopeptide, a fragment thereof, or a fusion protein as described above, which upon administration, is capable of reducing ameliorating or eliminating at least one symptom of multiple sclerosis. Further, effective amount means an amount capable of reducing or preventing multiple sclerosis condition.

Based on our previous work (Belogurov at al., The Journal of Immunology, 2008, 180: 1258-1267) the novel class of auto antibodies involved into recognition and degradation of Myelin Basic Protein in MS patients was discovered. These catalytically active antibodies represent very minor fraction of anti MBP antibodies, however it was found that their catalytic activity correlates with progressive state of MS. Thus, quantification of anti MBP autoantibody mediated MBP proteolysis was suggested as novel biomarker of MS. Surprisingly, despite ESAMBPCAA represent only minor fraction of circulating anti MBP auto antibodies in MS, the authors of present invention has discovered that certain oligopeptide, having strong neutralizing activity on ESAMBPCAA, demonstrate unexpectedly high efficacy in treatment of MS both in humans and in well-established animal models of multiple sclerosis. According to the present invention there an oligopeptide having amino acid sequence GGDRGAPKRGSGKDSHH (SEQ ID NO: 2) is provided. This sequence corresponds to amino acid sequence 46-62 of human MBP and is referred hereinafter as "MBP 46-62". Said oligopeptide is capable of inhibiting ESAMBPCAA.

Fragments and functional variants of oligopeptide GGDRGAPKRGSGKDSHH SEQ ID NO: 2) constitute one of preferred embodiments of present invention. On the basis of the ESAMBPCAA inhibition assays using a series of truncated forms of oligopeptide GGDRGAPKRGSGKDSHH (SEQ ID NO: 2) the smallest number of amino acids required for oligopeptide fragment to retain its biological activity were established. Thus, according to the present invention, the fragment or functional variant of an oligopeptide GGDRGAPKRGSGKDSHH (SEQ ID NO: 2) must retain at least 6 contiguous amino acid residues of SEQ ID NO: 2. Based on given disclosure, it would be readily apparent to persons skilled in the art to determine, empirically, what variation can be made to the oligopeptide sequence GGDRGAPKRGSGKDSHH (SEQ ID NO: 2) without affecting the ESAMBPCAA inhibitory activity of the peptide.

In another aspect, the present invention provides two oligopeptides having sequences GFGYGGRASDYKSAHK (SEQ ID NO: 3) and QGTLSKIFKLGGRDSRSGSPMARR (SEQ ID NO 4), respectively. These peptides contains well known in the art MBP epitopes, recognized by immune T-cells and/or by "conventional" (non-proteolytic) anti MBP auto antibodies from MS patients. The inventors have unexpectedly found that these two oligopeptides (SEQ ID NO: 3 and SEQ ID NO: 4 synergistically enhance efficacy of the oligopeptide (SEQ ID NO: 2) of present invention in treatment of multiple sclerosis in humans and preventing (or reducing) development of established animal model of MS-experimental allergic encephalomyelitis (EAE). Despite having low inhibitory activity against ESAMBPCAA as compared to oligopeptide (SEQ ID NO: 2), these two oligopeptides potentiate therapeutic effect of GGDRGAPKRGSGKDSHH (SEQ ID NO: 2) oligopeptide when co-administered to animals and humans. While not wishing to be bound by any theory, it may be assumed that this is due to fact that simultaneous modulation of several immune mechanisms—immune T cell function and auto antibody mediated MBP hydrolysis may provide multiplication of therapeutic effect. Accordingly, a pharmaceutical composition is provided which contains the oligopeptide of SEQ ID NO: 2, fragments or functional variants thereof and at least one of two oligopeptides of sequences SEQ ID NO: 3 or SEQ ID NO: 4.

In a further embodiment of the present invention, the oligopeptides of SEQ ID NO: 2, fragments or functional variants thereof are linked to each other to form a fusion peptide. Such fusion peptide comprises multiple copies of ESAMBPCAA inactivating moiety.

In a further embodiment of the present invention oligopeptide (SEQ ID NO: 2) or fragments or functional analogs thereof and oligopeptide (SEQ ID NO: 3) or fragments thereof and oligopeptide (SEQ ID NO: 4) or fragments thereof are linked to linked to each other in any order to form the fusion peptide, Thus, a fusion peptide of present invention may contain multiple repetitive copies of ESAMBPCAA inactivating moieties of oligopeptide (SEQ ID NO: 2) and epitopes of oligopeptides (SEQ ID NO: 3) and (SEQ ID NO: 4).

The invention further provides a pharmaceutical composition comprising therapeutically effective amount of an oligopeptide of present invention (SEQ ID NO: 2) or fragment or functional variant thereof or fusion protein and a pharmaceutically acceptable carrier or a diluent and/or drug delivery system. Examples of pharmaceutical acceptable carriers are well known in the art, and include for example normal saline. The examples of drug delivery systems are also well known in the art and include for example liposomes or synthetic polymeric nanoparticles. The oligopeptides of the present invention can be prepared according to existing methods of synthesizing oligopeptides having formula according disclosure provided. Fusion proteins may be produced by recombinant DNA technology. Knowing the sequence of the selected fusion proteins, as disclosed in the present invention, the appropriate DNA sequence can be produced by conventional, known methods of synthesizing DNA sequences. The DNA sequences so produced can then be cloned into appropriate cloning vehicles and used to transform an appropriate host cell to produce the recombinant peptide. All of the methodology referred to above is conventional and well-known to persons skilled in the art.

The invention further provides a method for treating multiple sclerosis, the method comprising administering an effective dose of oligopeptide, or a fragment, or fusion peptide, or a pharmaceutical composition containing same to a subject in need thereof. The therapeutic dose of oligopeptides or fusion protein for the treatment of MS may be from about 0.01 mg per kilogram of body weight to about 10.0 mg per kilogram of body weight; the composition can be administered intravenously, subcutaneously, intrathecally. In one example of the present invention, the composition is administered orally, to target so called "mucosal delivery route". The composition can be administered as a single or sequential dose, as may be required.

While this invention is described in detail with particular reference to preferred embodiments thereof, the following examples are offered to illustrate but not limit the invention.

EXAMPLES

Example I. Detection of ESAMBPCAA-Autologous Immunoglobulin Molecules which Binds Myelin Basic Protein and Catalyze Site-Specific Proteolytic Cleavage of the MBP Molecule in Blood of Multiple Sclerosis Patients Anti MBP autoantibody purification and characterization were done using the serum of 24 MS patients (17-54-year-old, mean age 32 years) who had not been treated with steroids or non-steroidal anti-inflammatory drugs. The MS diagnosis was verified and confirmed, and EDSS (Expanded Disability Status Scale) values were calculated according to Poser's classification of disease progression, using clinical, immunological and MRI data (Poser et al., Clin Neurol Neurosurg 2001; 103:1-11). Immunoglobulins (IgG) were isolated from serum by thrice-repeated 50% ammonium sulfate precipitation followed by affinity chromatography on protein G-Sepharose (Amersham Biosciences). IgG-containing fractions were then dialyzed against PBS or TBS with 0.05% NaN$_3$ at 4° C. The IgG amount was quantified and standardized by ELISA. IgG purity was assessed by electrophoresis followed by silver staining, immunoblotting under nonreducing conditions and by surface-enhanced laser desorption/ionization (SELDI) mass spectrometry. IgGs were further separated by the antigen affinity chromatography on a column with MBP immobilized on NHS-Sepharose (Amersham) and their purity was assessed by electrophoresis followed by silver staining technique.

MBP was prepared from bovine brain according to Miller (Miller et al., 1996. Experimental autoimmune encephalomyelitis in the mouse. In: Current Protocols in Immunology; J. E. Coligan, ed. Wiley, New York, p. S19.) The resulting protein was purified by reverse phase HPLC on column C4 10/250 (Mashery-Nagel, Germany).

MBP hydrolysis by anti MBP auto antibodies was assayed as follows: Purified antibodies (0.1-1 μg) were incubated at 37° C. for 14 h in the final volume of 12.5 μl PBS, 0.02% NaN$_3$ containing 1-2 μg of MBP. The samples were mixed with Laemmli's buffer. The extent of MBP degradation was visualized by SDS-PAGE in Tris-glycine and Tricine buffer systems. For quantitative MBP degradation assay, MBP (10 μM) was incubated at 37° C. with antibodies (60 nM) in 0.1 ml of PBS, 0.02% NaN$_3$ for 12 h. The reaction was stopped by adding 10% TFA up to pH 2.5. The samples were further chromatographed on column C4 4.0/150 (Waters). The amount of non-cleaved MBP was calculated by absorbance monitoring at 280 nm.

The results are presented in Table 1.

TABLE 1

Clinical statuses of 24 multiple sclerosis patients and corresponding rates of MBP hydrolysis by ESAMBPCAA.

| Patient N | Type of disease | ESAMBPCAA activity (pmol/min/nmol) | EDSS score |
|---|---|---|---|
| MS1 | SP | 77.6 ± 7.1 | 5.0 |
| MS2 | SP | 84.3 ± 6.9 | 4.5 |
| MS3 | SP | 63.0 ± 5.8 | 6.0 |
| MS4 | RR | 45.6 ± 6.0 | 2.0 |
| MS5 | RR | 5.9 ± 4.8 | 1.0 |
| MS6 | RR | 2.1 ± 4.5 | 1.0 |
| MS7 | RR | 5.3 ± 5.0 | 2.0 |
| MS8 | RR | 3.0 ± 3.9 | 1.5 |
| MS9 | SP | 71.2 ± 5.5 | 3.0 |
| MS10 | SP | 4.5 ± 4.1 | 2.5 |
| MS11 | RR | 1.5 ± 6.0 | 0 |
| MS12 | SP | 79.0 ± 8.9 | 4.0 |
| MS13 | RR | 2.0 ± 4.0 | 0 |
| MS14 | PP | 44.9 ± 5.0 | 3.0 |
| MS15 | PP | 22.3 ± 4.5 | 3.0 |
| MS16 | RR | 29.3 ± 5.3 | 2.5 |
| MS17 | RR | 15.1 ± 4.1 | 3.0 |
| MS18 | RR | 4.3 ± 3.9 | 1.5 |
| MS19 | RR | 6.5 ± 4.0 | 2.0 |
| MS20 | SP | 15.0 ± 5.9 | 3.0 |
| MS21 | SP | 1.3 ± 3.7 | 2.0 |
| MS22 | RR | 39.2 ± 7.2 | 3.0 |
| MS23 | SP | 29.1 ± 6.2 | 3.0 |
| MS24 | RR | 4.3 ± 3.5 | 1.5 |

SP—secondary progressive; PP—primary progressive; RR—relapsing-remitting.

Importantly, the level of the ESAMBPCAA mediated MBP cleavage correlated with expanded disability status scale (EDSS) range of the patients (r2=0.85, P<0.001 by Spearman rank correlation). The highest levels of the antibody mediated catalysis occurred in cases with high EDSS (from 3.0 to 6.0), mostly at the progression stage or the exacerbation at the relapsing-remitting (RR) course of the disease.

Example 2. Screening for ESAMBPCAA Inhibitory Sequences

Twelve DNA fragments encoding human MBP peptides representing different parts of MBP molecule (1-27, 17-41, 25-54, 43-68, 53-81, 81-103, 91-114, 107-132, 123-140, 130-156, and 146-170, were prepared by PCR with four overlapping corresponding to the linker (SGGGG)3S (SEQ ID NO: 9). The final PCR products were cloned in-frame into pET32CH plasmid by using NcoI and BamHI restriction sites. The expression products of these plasmids that contained Trx fused to MBP peptides were used for cleavage analysis. The plasmid encoding Trx (Thioredoxin) with linker (SGGGG) 3S (SEQ ID NO: 9) was designed for control. The soluble recombinant His-tagged proteins were obtained by *Escherichia coli* expression and isolated by sorption on Talon SuperFlow (BD Biosciences) column, followed by cation exchange chromatography on Mono S column (Amersham Pharmacia) at pH 5.0 and subsequent size exclusion chromatography on Superdex 75 GL 10_300 column (Amersham Pharmacia) in 150 mM NH$_4$HCO$_3$ buffer.

Pattern of MBP hydrolysis by ESAMBPCAA purified from plasma of SJL mice suffering from EAE, induced by injection of MBP in complete Freund adjuvant, was assessed by SDS-PAGE as specified in Example 1 in presence of 0.5 mkM of different MBP peptides. The results are presented in FIG. 2. The MBP fragment 43-68, which contains sequence GGDRGAPKRGSGKDSHH (SEQ ID NO: 2), demonstrates potent inhibitory activity on anti MBP auto antibody mediated MBP hydrolysis.

Example 3. Suppression of MBP-Specific Auto Antibody Mediated Hydrolysis by Synthetic Oligopeptides Containing Amino Acid Sequences of MBP Fragment 43-68

In order to identify the amino acid sequence required for efficient inhibition of ESAMBPCAA activity the following series of peptides were synthesized:

TABLE 2

| | SEQ ID NO: | Amino acid sequence | Number of amino acid residues | Position in MBP sequence |
|---|---|---|---|---|
| A1 | 10 | RFFGGDRGAPKRGSGKDSHHPARTAH | 26 | 43-68 |
| A2 | 11 | FGGDRGAPKRGSGKDSHHPAR | 21 | 45-65 |
| A3 | 2 | GGDRGAPKRGSGKDSHH | 17 | 46-62 |
| A4 | 12 | GAPKRGSGKDSHH | 13 | 50-62 |
| A5 | 13 | GGDRGAPKRGS | 11 | 46-56 |
| A6 | 14 | PKRGSGKDSHH | 11 | 52-62 |
| A7 | 15 | GGDRGAPKR | 9 | 46-54 |
| A8 | 16 | RGSGKDSHH | 9 | 54-62 |
| A9 | 17 | GGDRGAP | 7 | 46-52 |
| A10 | 18 | SGKDSHH | 7 | 56-62 |
| A11 | 19 | GGDRG | 5 | 46-50 |
| A12 | 20 | KDSHH | 5 | 58-62 |

Figure 3:
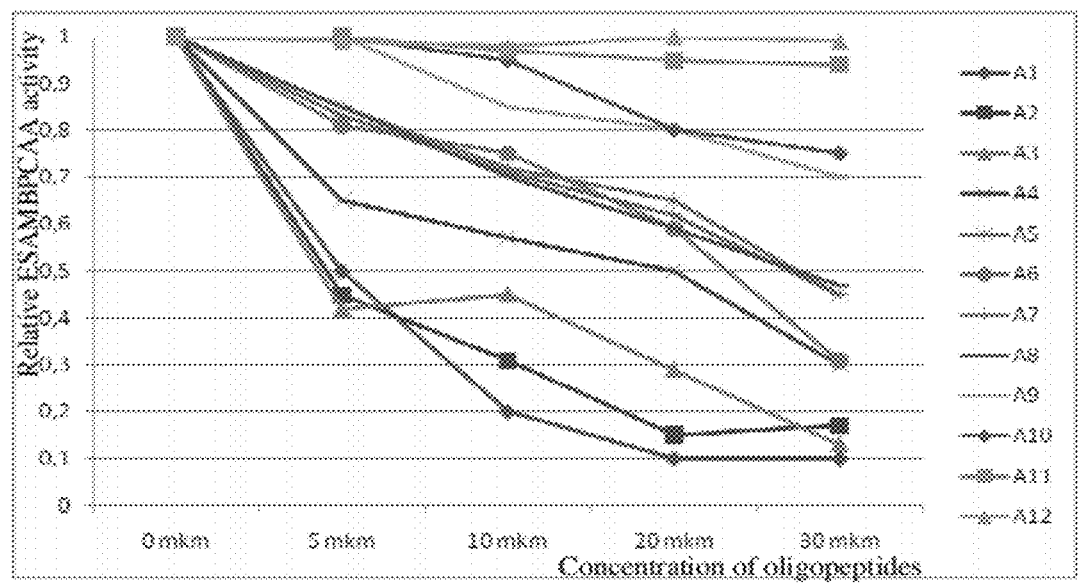
FIG. 3 illustrates the inhibition of ESAMBPCAA activity by different synthetic oligopeptides containing amino acid sequences of MBP fragment 43-68. Horizontal axis—concentration of oligopeptides used in inhibitory assay; Vertical axis—relative ESAMBPCAA activity (ESAMBPCAA activity in control assays (PBS) were deemed as 1). Codes of oligopeptides are indicated in Example 3.

The oligopeptides were assayed for their potency to inhibit ESAMBPCAA mediated MBP hydrolysis using ESAMBPCAA collected from progressive MS Patient as specified in Example 1. Different concentrations of test peptides were mixed with both antibodies (30 nM) and MBP (4 mkM) in TBS with_0.1% NaN3_and 10 mM CaCl2. The samples were incubated for 16 h at 37° C. and analyzed on 15% SDS_PAGE. The gels were stained by Coomassie and analyzed by densitometry with TOTALLAB 2.01 software (Nonlinear Dynamics, Ltd., Newcastle upon Tyne, U.K.). The data presented in FIG. 3 shows that from tested oligopeptides the oligopeptide A3, comprising amino acid sequence GGDRGAPKRGSGKDSHH (SEQ ID NO: 2) demonstrates most potent inhibitory activity, having less amino acid residues than oligopeptides A1 and A2. Shortening of oligopeptide lengths to less than 6 amino acids lead to complete lack of ESAMBPCAA inhibitory activity.

Example 4. Suppression of MBP-Specific Auto Antibody Mediated Hydrolysis by Synthetic Oligopeptides Containing Amino Acid Sequence GGDRGAPKRGSGKDSHH (SEQ ID NO: 2), Fragments Thereof and Fusion Proteins.

Serum samples collected from 5 patients suffering from progressive MS were quantified for ESAMBPCAA mediated MBP hydrolysis as specified in Example 1 in presence of following substances:

A1—negative control: phosphate buffered saline (PBS);

A2—glatiramer acetate (Copaxone, Teva Pharmaceuticals), 100 nM;

A3—oligopeptide GGDRGAPKRGSGKDSHH (SEQ ID NO: 2) 100 nM;

A4—oligopeptide APKRGSGKDSH (SEQ ID NO: 23) (a fragment of oligopeptide GGDRGAPKRGSGKDSHH (SEQ ID NO: 2)—100 nM;

A5—oligopeptide SGKDS (SEQ ID NO: 26) (a fragment of oligopeptide GGDRGAPKRGSGKDSHH (SEQ ID NO: 2))—100 nM;

A6—fusion protein RGAPKRGSGKRGAPKRGSGKRGAPKRGSGKRGAPKRGSGKRGAPKRGSGKRGAP-KRG SGK (SEQ ID NO: 21) (containing repetitive sequence RGAPKRGSGK (SEQ ID NO: 22), which sequence represents the fragment of GGDRGAPKRGS-GKDSHH (SEQ ID NO: 2) oligopeptide—100 nM);

The products A3, A4 and A5 have been synthesized by the laboratory of solid phase organic synthesis (Shemyakin Ovchinnikov Institute of Bioorganic Chemistry RAS. The product A6 has been synthesized using ABNOVA custom cell-free translation system. (www.abnova.tw).

The results of the assay are presented in Table 3 below.

TABLE 3

Influence of different tested preparations on MBP-specific auto antibody mediated hydrolysis (pmol/min/nmol)

| | Patient 1 | Patient 2 | Patient 3 | Patient 4 | Patient 5 |
|---|---|---|---|---|---|
| A1 (PBS) | 77.6 ± 7.1 | 84.3 ± 6.9 | 63.0 ± 5.8 | 45.6 ± 6.0 | 79.0 ± 8.9 |
| A2 | 62.5 ± 1.2 | 72.6 ± 7.7 | 51.2 ± 3.5 | 47.7 ± 7.9 | 65.7 ± 5.4 |
| A3 | 11.2 ± 3.5 | 17.3 ± 4.1 | 14.4 ± 2.2 | 14.5 ± 4.4 | 16.9 ± 7.3 |
| A4 | 12.1 ± 3.6 | 15.6 ± 2.9 | 14.3 ± 4.4 | 15.8 ± 4.9 | 13.3 ± 5.9 |
| A5 | 57 ± 4.1 | 59.7 ± 5.7 | 44.2 ± 6.6 | 45.5 ± 3.8 | 55.7 ± 6.1 |
| A6 | 7.7 ± 3.3 | 22.3 ± 4.2 | 20.1 ± 3.9 | 21.5 ± 6.6 | 5.0 ± 1.8 |

Thus, oligopeptide GGDRGAPKRGSGKDSHH (SEQ ID NO: 2), oligopeptide APKRGSGKDSH (SEQ ID NO: 23) (a fragment of oligopeptide GGDRGAPKRGSGKDSHH (SEQ ID NO: 2) with 11 amino acids length and the fusion protein containing repetitive sequence RGAPKRGSGK (SEQ ID NO: 22), which sequence represents the fragment of GGDRGAPKRGSGKDSHH (SEQ ID NO: 2) oligopeptide all has potent suppressive effect on MBP-specific auto antibody mediated hydrolysis

Example 5

Treatment of EAE by the Inventive Oligopeptide and the Fusion Protein

Experimental Allergic Encephalomyelitis (EAE) in DA rats is well established animal model of MS. The animal work was performed in the Pushchino branch of the Shemyakin and Ovchinnikov Institute of Bioorganic Chemistry, Russian Academy of Sciences. Female DA rats 10-14 weeks of age were anesthetized and injected intradermally at the base of the tail with 100 ml of inoculums containing 50 mg of rat MOG in saline emulsified (1:1) with CFA (Sigma Chemical Co., St. Louis, Mo.) containing 200 mg of *Mycobacterium tuberculosis* (strain H 37 RA; Difco Laboratories, Detroit, Mich.). At day 8 after a second immunization, rats were divided into 6 groups (6 rats per group) and treated during 5 days (days 8-12) according following schedule:

Group 1—oligopeptide GGDRGAPKRGSGKDSHH (SEQ ID NO: 2) at 120 µg daily by intranasal administration Group 1—oligopeptide GGDRGAPKRGSGKDSHH (SEQ ID NO: 2) at 50 µg daily by intranasal administration Group 3—fusion protein RGAPKRGSGKRGAPKRGS-GKRGAPKRGSGKRGAPKRGSGKRGAPKRG SGK (SEQ ID NO: 21) at 120 µg daily by intranasal administration Group 4—oligopeptide APKRGSGKDSH (SEQ ID NO: 23) at 120 µg daily by intranasal administration Group 5—Glatiramer acetate (Copaxone, Teva) 120 µg daily by intranasal application Group 6—Control (PBS)

Clinical symptoms (MDS score) of disease were assessed daily on the following grading scale: grade 0, no clinical signs; grade 1, mild waddling gait or flaccid tail; grade 2, severe waddling gait; grade 3, moderate hind limb paresis; and grade 4, severe hind limb paralysis. Serum samples collected from animals were quantified for ESAMBPCAA mediated MBP hydrolysis as specified in Example 1

Figure 4:
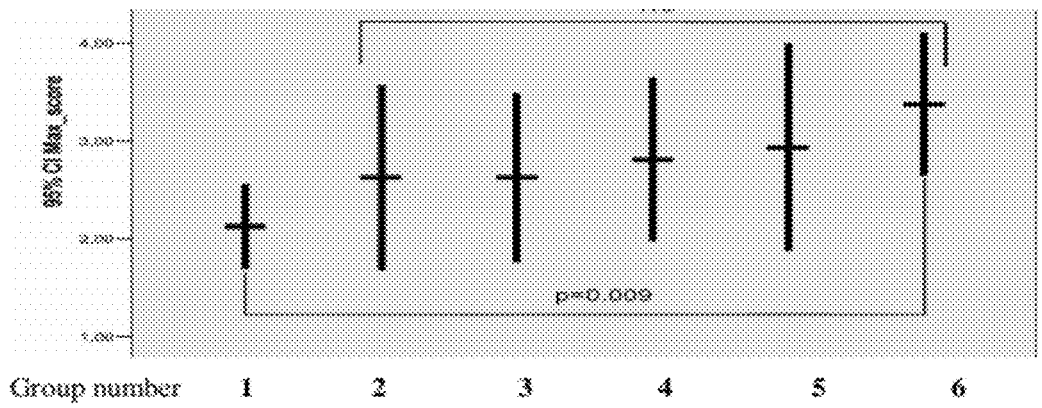
FIG. 4 illustrates suppression of MDS score of DA rats suffering from Experimental Allergic Encephalomyelitis and treated by inventive oligopeptides and the fusion protein. Suppression of MDS score in ongoing EAE in DA rats at day 24. Maximum clinical score in each group of rats, median and 95% confidential interval.

The results are presented at FIG. 4 and Table 4 below.

TABLE 4

Influence of treatment on rates of MBP-specific auto antibody mediated hydrolysis (Median for 6 animals; pmol/min/nmol)

| Experimental Group | Day 8 | Day 16 | Day 24 |
|---|---|---|---|
| Group 1 | 42.8 ± 5.5 | 17.3 ± 5.4 | 15.1 ± 3.9 |
| Group 2 | 43.1 ± 6.4 | 35.6 ± 4.9 | 46.3 ± 2.9 |
| Group 3 | 45.7 ± 6.5 | 48.1 ± 7.4 | 39.4 ± 4.6 |
| Group 4 | 49.3 ± 4.9 | 45.9 ± 7.1 | 45.1 ± 6.3 |
| Group 5 | 51.4 ± 8.2 | 55.4 ± 5.7 | 62.2 ± 5.7 |
| Group 6 | 47.6 ± 6.1 | 61.3 ± 7.35 | 75.2 ± 8.3 |

Thus, both the MBP-specific auto antibody mediated hydrolysis and MDS score are most efficiently suppressed by oligopeptide GGDRGAPKRGSGKDSHH (SEQ ID NO: 2) in the dose-dependent manner. Fusion protein RGAP-KRGSGKRGAPKRGSGKRGAPKRGSGKRGAPKRGS-GKRGAPKRGSGKRGAPKRG SGK (SEQ ID NO: 21) and oligopeptide APKRGSGKDSH (SEQ ID NO: 23) are also active in suppression of MBP-specific auto antibody mediated hydrolysis and MDS score.

Example 6

Treatment of Experimental MS (Theiler's Virus Infection) with Inventive Oligopeptides and Combinations of Oligopeptides The BeAn strain of TMEV used in this study was generated and propagated in BHK-21 cells grown in Dulbecco's modified Eagle's medium supplemented with 7.5% donor calf serum. For i.c. infection, 30 µl of virus solution ($0.2 \times 10^6$ to $6 \times 10^6$ PFU) was injected into the right cerebral hemisphere of 6- to 8-week-old SJL mice (8 animals per group) anesthetized with isoflurane. Clinical symptoms (MDS score) of disease were assessed weekly on the following grading scale: grade 0, no clinical signs; grade 1, mild waddling gait or flaccid tail; grade 2, severe waddling gait; grade 3, moderate hind limb paresis; and grade 4, severe hind limb paralysis. Serum samples collected from animals were quantified for ESAMBPCAA mediated MBP hydrolysis as specified in Example 1

Oligopeptides GFGYGGRASDYKSAHK (SEQ ID NO: 3) and QGTLSKIFKLGGRDSRSGSPMARR (SEQ ID NO: 4) are known in the art as capable to modulate immune T cell activity in MS, leading to some efficacy in treatment of MS.

At day 14 following infection mice were divided into 6 groups (30 mice per group) and treated during 10 days (days 14-24) according following schedule:

Group 1—Control—PBS daily by subcutaneous injection

Group 2—Copaxone daily 30 µg daily by subcutaneous injection

Figure 5:
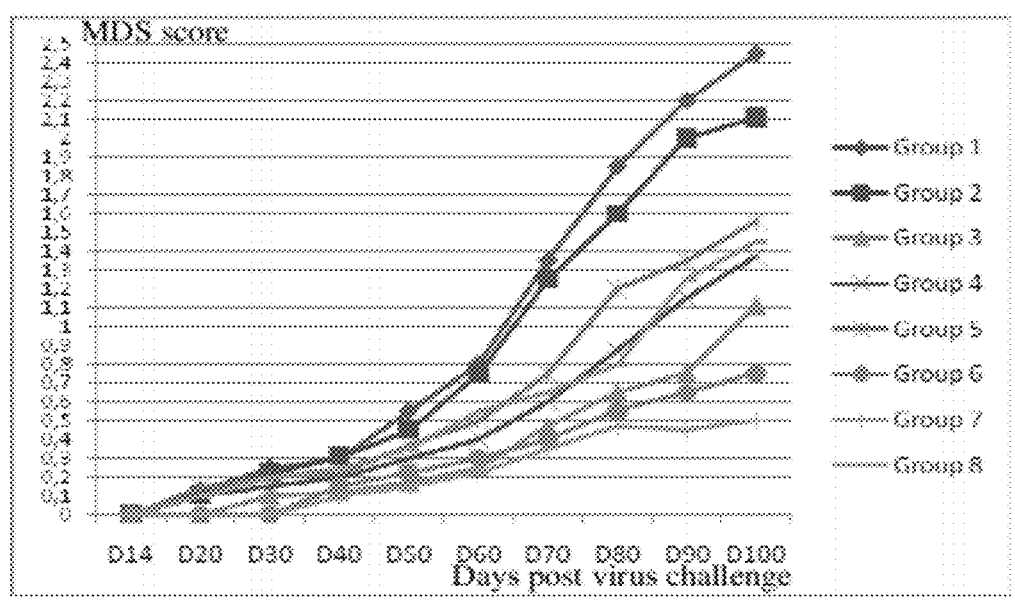
FIG. 5 illustrates suppression of MDS score in ongoing experimental MS (Theiler's Virus Infection) with combinations of oligopeptides.

Group 3—Oligopeptide GGDRGAPKRGSGKDSHH SEQ ID NO: 2) at 20 µg daily by subcutaneous injection Group 4—Oligopeptide GFGYGGRASDYKSAHK (SEQ ID NO: 3) at 20 µg daily by subcutaneous injection Group 5—Oligopeptide QGTLSKIFKLGGRDSRSGSP-MARR (SEQ ID NO: 4) at 20 µg daily by subcutaneous injection Group 6—Oligopeptide GGDRGAPKRGSGKDSHH (SEQ ID NO: 2) at 20 µg and oligopeptide GFGYGGRASDYK-SAHK (SEQ ID NO: 3) at 20 µg daily by subcutaneous injection Group 7—Oligopeptide GGDRGAPKRGSGKDSHH (SEQ ID NO: 2) at 20 µg and oligopeptide GFGYGGRASDYK-SAHK (SEQ ID NO: 3) at 20 µg and oligopeptide QGTL-SKIFKLGGRDSRSGSPMARR (SEQ ID NO: 4) at 20 µg daily by subcutaneous injection Group 8—Oligopeptide GFGYGGRASDYKSAHK (SEQ ID NO: 3) at 20 µg and oligopeptide QGTLSKIFKLGGRD-SRSGSPMARR (SEQ ID NO: 4) at 20 µg daily by subcutaneous injection The results are presented at FIG. 5 and Table 5 below.

TABLE 5

Influence of performed treatment on disease manifestation and rates of auto antibody mediated MBP hydrolysis.

| Group | % Animals affected with disease at day 100 | ESAMBPCAA activity at day 100 (pmol/min/nmol) |
|---|---|---|
| Group 1 | 27(30) | 45.7 ± 6.7 |
| Group 2 | 25(30) | 39.8 ± 4.1 |
| Group 3 | 19(30) | 11.4 ± 3.5 |
| Group 4 | 25(30) | 40 ± 3.1 |
| Group 5 | 27(30) | 35.3 ± 5.1 |
| Group 6 | 15(30) | 16.5 ± 3.2 |
| Group 7 | 17(30) | 14.1 ± 2.9 |
| Group 8 | 25(30) | 37.7 ± 4.9 |

Thus, MBP-specific auto antibody mediated hydrolysis and MDS score are most efficiently suppressed by oligopeptide GGDRGAPKRGSGKDSHH (SEQ ID NO: 2) alone or in combination with oligopeptide GFGYGGRASDYKSAHK (SEQ ID NO: 3) and/or oligopeptide QGTLSKIFKLGGRDSRSGSPMARR (SEQ ID NO: 4).

Oligopeptides GFGYGGRASDYKSAHK (SEQ ID NO: 3) and oligopeptide QGTLSKIFKLGGRDSRSGSPMARR (SEQ ID NO: 4) alone or in combination has moderate therapeutic effect and do not affect MBP-specific auto antibody mediated hydrolysis. Combination of GGDRGAPKRGSGKDSHH (SEQ ID NO: 2) with GFGYGGRASDYKSAHK (SEQ ID NO: 3) and QGTLSKIFKLGGRDSRSGSPMARR (SEQ ID NO: 4) has most beneficial therapeutic effect. Importantly, peptide GGDRGAPKRGSGKDSHH (SEQ ID NO: 2) and its combinations with oligopeptide GFGYGGRASDYKSAHK (SEQ ID NO: 3) and/or oligopeptide QGTLSKIFKLGGRDSRSGSPMARR (SEQ ID NO: 4) have also disease-preventive (prophylactic) activity.

Example 7

Suppression of MBP-Specific Auto Antibody Mediated Hydrolysis and Treatment of MS by Means of Exposing the Blood of Patient to the Fusion Proteins According the Invention:

Three fusion proteins of the following formulas were synthesized using ABNOVA custom cell-free translation system (www.abnova.tw):

```
1)                                           (SEQ ID NO: 21)
RGAPKRGSGKRGAPKRGSGKRGAPKRGSGKRGAPKRGSGKRGAPKRGSGKR

GAPKRGSGK 2)                                           (SEQ ID NO: 24)
GAPKRGSGKYGGRASDYKSGTLSKIFKLGGRDSRRGAPKRGSGKYGGRASD

YKSGTLSKIFKLGGRDSR 3)                                           (SEQ ID NO: 25)
GGDRGAPKRGSGKDSHHGFGYGGRASDYKSAHKQGTLSKIFKLGGRDSRSG

SPMARR
```

Thus, these fusion proteins contain SEQ ID NO: 2, SEQ ID NO:3, SEQ ID NO:4 linked in a different order.

All three oligopeptides were coupled to CNBr-activated Sepharose beads (Pharmacia) at 0.1 mg of each oligopeptide per 1 ml beads under aseptic conditions. After coupling, the oligopeptide-Sepharose was washed extensively with 0.01M Tris-buffered 1.14 M NaCl, pH 8.0 containing 10 mM EDTA to remove noncovalently associated material and packed into 400 ml columns.

The case of ESAMBPCAA apheresis was performed in St. Petersburg Medical Academy, Department of Neurology. We performed the ESAMBPCAA apheresis in 18-year old patient with rapidly progressing severe secondary progressive MS, deemed being resistant to conventional therapy (corticosteroids and immunosuppressants). The patient underwent 5 apheresis cycles, one cycle per week. Patient plasma was separated by a continuous-flow plasma separator, the Cobe Spectra, USA. The blood flow varied from 50 to 70 ml/min. Heparin was also added with an initial bolus of 5000 U, then, in the first phase, 50 U/min by the pump. Plasma was than washed through the Sepharose column, and the rest of blood was returned to the patient. The flow of plasma through the Sepharose column was controlled by a computerized adsorption-desorption device ADA—Medicap. Following passage through the column the plasma returned to the patient. In each cycle 3000 ml of plasma was treated. The EDSS score dropped from 6 before the first apheresis to 5.5 two weeks after the last cycle. The control MRI performed one month after the last cycle showed stabilization of the previous lesions with the reduction of two lesions. No new lesions were detected. The rate of MBP-specific auto antibody mediated hydrolysis was assayed as specified in Example 1 before and two weeks after the last apheresis cycle. The data is presented in the Table 6 below.

TABLE 6

Suppression of MBP-specific auto antibody mediated hydrolysis under the treatment performed.

| Parameter | Before therapy | 2 weeks following last cycle |
|---|---|---|
| ESAMBPCAA | 87 pmol/min/nmol | 15 pmol/min/nmol |
| IgG | 410 mg/dL | 395 mg/dL |
| IgA | 53 mg/dL | 57 mg/dL |
| IgM | 24 mg/dL | 22 mg/dL |
| EDSS score | 6 | 5.5 |

Thus, exposing the blood of MS patient to fusion proteins according the invention suppresses ESAMBPCAA activity and provides effective treatment for MS.

Also, certain other fusion proteins containing SEQ ID NO: 2, SEQ ID NO:3, SEQ ID NO:4 linked in other order (via peptide and non-peptide linkers) were produced and successfully tested for ESAMBPCAA suppressing activity and ability to ameliorate MS symptoms and to decrease MS biomarker.

Example 8

Pharmaceutical Composition Containing Fragments of Oligopeptide

The three oligopeptides of following formulas: GGDRGAPKRGSGKDSHH (SEQ ID NO: 2), GFGYGGRASDYKSAHK (SEQ ID NO: 3) and QGTLSKIFKLGGRDSRSGSPMARR (SEQ ID NO: 4) have been synthesized by the laboratory of solid phase organic synthesis (Shemyakin Ovchinnikov Institute of Bioorganic Chemistry RAS); phospholipids were purchased from Sigma—Aldrich and Avanti Polar Lipids. 50 g of mixture of egg phosphatidylcholine (PC), Dioleoyl phosphatidylcholine (DOPE) and 1, 2-dioleoyl-3-trimethylammonium-propane (DOTAP) (at 4:2:1 molar ratio) was dissolved in chloroform and then chloroform was removed by evaporation. Oligopeptides 1, 2 and 3 were dissolved in phosphate buffered saline (PBS), PH7, 4 at 5 g/L concentration of each individual oligopeptide (15 g/L total protein). The lipid film in the evaporation vessel was rehydrated by mixing with 10 liters of PBS-peptides solution and 30 min shaking at 40° C. The resulting lipid/protein emulsion was transferred to 10 ml vials and lyophilized. The dry powder was solubilised "ex-tempore" with 5 ml of water for injection (WFI) to form large multi-lamellar liposomes (LMV) containing the oligopeptides.

Example 9

Treatment of Patients with Relapsing Remitting MS with Oral Liposomal Formulation of Oligopeptides The trial was performed between April 2003 and June 2005 in St. Petersburg Medical Academy, Department of Neurology. Under the approval of local Ethics Committee totally 15 patients (5 male and 10 female with median age of 32 years) with relapsing-remitting MS (diagnosed according Poster and MacDonald criteria) with at least two documented relapses within two last years and having EDSS (Kurtzke Expanded Disability Status Scale) score from 0 up to 5.5 were recruited to the trial.

Patients were treated by daily oral dosing of liposomes (LMV), manufactured as described in Example 8 at 0.5 mg of protein per kg of body weight. The treatment was performed as monotherapy continuously daily for the period of 2 years.

EDSS scoring were checked once every two month. Brain MRT check for active demyelinization locuses (ADL) was performed once every two month. Analysis of frequency and duration of relapses was performed at the end of 2-year observation period. Blood cell counts, ESAMBPCAA activity, blood biochemistry and immunological parameters were checked at the beginning and the end of the trial.

All 15 patients have stable EDSS score within first 6 month of treatment. The average frequency of relapses decreased from 2.7 per year at inclusion to 1.5 per year at the end of treatment period. During 2 year follow-up period 11 patients were relapse-free. 6 patients (40%) have less ADL at the end of treatment period. 7 patients (47%) have process stabilization—the same number of ADL. In 2 patients (13%) the ADL count has increased. No adverse events linked to investigational preparation were noted. The immunological parameters, blood biochemistry and blood cell counts were not significantly changed at the end of treatment period. The data is presented in Table 7.

TABLE 7

Immunological, blood and blood biochemistry parameters at the beginning and at the end of treatment (data average for 15 patients)

| Parameter | Before treatment | After treatment |
|---|---|---|
| CD3 | 48.75 ± 9.68 | 52.37 ± 7.37 |
| CD4 | 29.75 ± 6.43 | 30.25 ± 4.06 |
| CD8 | 22.87 ± 5.34 | 25.5 ± 6.2 |
| CD4/CD8 | 1.37 ± 0.29 | 1.29 ± 0.35 |
| IgA | 2.88 ± 1.53 | 2.77 ± 1.46 |
| IgM | 1.59 ± 0.71 | 1.68 ± 0.41 |
| IgG | 19.67 ± 6.45 | 16.00 ± 5.10 |
| HLADR | 23.13 ± 5.38 | 21.25 ± 5.88 |
| ESAMBPCAA | 45.1 ± 6.2 | 12.5 ± 4.5 |
| HB | 128.86 ± 14.73 | 126.57 ± 20.08 |
| WBC | 5.69 ± 1.38 | 5.04 ± 0.98 |
| Lymphocytes % | 28.29 ± 8.94 | 25.36 ± 5.12 |
| ALT | 0.29 ± 0.20 | 0.21 ± 0.07 |
| AST | 0.25 ± 0.12 | 0.19 ± 0.06 |
| Bilirubin | 12.36 ± 4.17 | 10.39 ± 2.67 |
| Urea | 3.62 ± 1.67 | 4.11 ± 1.16 |
| Creatinine | 0.07 ± 0.02 | 0.08 ± 0.01 |

Lower rate of MBP-specific auto antibody mediated hydrolysis was noted and that was in coincidence with significant curative effect achieved. Thus, the oral intake of oligopeptides according to present invention has favorable therapeutic performance associated with decrease of ESAMBPCAA activity. Under comparison with retrospective data available, results of treatment according the present invention shows better results than those of Beta-Interferon, which is existing standard of MS therapy. The comparison table 8 is presented below.

TABLE 8

Comparative data on clinical efficacy of currently available standard treatment regimes of MS and results of treatment according Example 8.

| Treatment | Clinical Observations | MRI Data: decrease of active lesions | Adverse Reactions | Reference |
|---|---|---|---|---|
| Copolymer 1 | Decrease of relapse frequency—29%; Slowing EDSS score progression | No statistical significant decrease | Low | Johnson K P, Brooks B R, Cohen J A, Ford C C, Goldstein J, Lisak P P et al. Copolymer-1 reduces relapse rate and improves disability in relapsing-remitting multiple sclerosis: Results of a phase III multicentre, double-blind, placebo controlled trial. The copolymer-1 multiple sclerosis study group. Neurology 1995; 45: 1268. |
| Beta-Interferon | Decrease of relapse frequency—83%; No slowing EDSS score progression | 83% decrease | High | Paty D W, Li D K B, the UBC MS/MRI Study Group and the Interferon Beta Multiple Sclerosis Study Group. Interferon beta-1b is effective in relapsing-remitting multiple sclerosis. II. MRI results of a multi-centred, double-blind, placebo-controlled trial. Neurology 1993; 43: 662-7 |
| Oligopeptides according the invention | Decrease of relapse frequency—87%; Slowing EDSS score progression | 75% decrease | No | Example 8 |

Example 10

Female Dark Agouti (DA) Rats, 8-9 weeks of age, about 110-145 g of weight were used as test animals.

For induction of Experimental Allergic Encephalomyelitis (EAE), rats were injected intradermally at the base of the tail with a total volume of 200 µl of inoculum containing 50 µg of MBP 63-81 (ANASPEC), in saline mixed (1:1) with Complete Freund Adjuvant, (IFA, Sigma), and 1 mg killed *M. tuberculosis* strain (strain H37 RA; Difco Laboratories, Detroit, Mich.). Beginning 24 hours after EAE induction the rats were followed up daily. On day 9 after the after EAE induction more than 50% of the rats developed signs of paralysis. The animals with multiple sclerosis signs were separated into 10 groups for beginning of treatment. Prior to treatment, blood was collected from 2 rats from each group. At day 9 and 11 after EAE induction, 90% of rats developed signs of EAE.

9-11 days after EAE induction the animals were divided into 9 groups (5-6 rats in each). Each group of rats was treated subcutaneously once daily with different claimed oligopeptide or theirs combinations (equimolar mix) (150 µg) or doses of positive control item (Glatiramer acetate, Copaxone, Teva) or negative control item (0.9% Sodium chloride solution), during 6 days as follows:

Group 1—Negative control (0.9% Sodium chloride solution);
Group 2—Positive control—(Copaxone)
Group 3—Oligopeptide GGDRGAPKRGSGKDSHH
Group 4—Oligopeptide GFGYGGRASDYKSAHK
Group 5—Oligopeptide QGTLSKIFKLGGRDSRSGSPMARR
Group 6—Equimolar mix (1:1; mol/mol) of oligopeptide GGDRGAPKRGSGKDSHH and oligopeptide GFGYGGRASDYKSAHK, correspondingly
Group 7—Equimolar 1 mix (1:1; mol/mol) of oligopeptide GGDRGAPKRGSGKDSHH and oligopeptide QGTLSKIFKLGGRDSRSGSPMARR
Group 8—Equimolar mix (1:1:1; mol/mol/mol) of oligopeptide GGDRGAPKRGSGKDSHH and oligopeptide GFGYGGRASDYKSAHK and oligopeptide QGTLSKIFKLGGRDSRSGSPMARR
Group 9—Equimolar mix (1:1; mol/mol) of oligopeptide GFGYGGRASDYKSAHK and oligopeptide QGTLSKIFKLGGRDSRSGSPMARR Copaxone, claimed oligopeptide and combinations thereof (Mechanical mix) were diluted with 0.9% Sodium chloride to a concentration of 450 µg/ml. Volume of 0.33 ml (150 µg/rat/day) was injected SC during 6 days.

After 6 days of the injections cycle the animals were maintained and followed up till day $28^{th}$ post EAE induction. Clinical signs score was performed daily during study periods. Animals were observed individually during all study periods. In cases of extended observation period clinical signs were recorded once daily. Observations included changes in the fur, eyes, respiratory rate, vocalization, paralysis, activity and behavior pattern. Score of paralysis signs related to MS of each animal was done daily (during all study periods).

Score gradation was as follows: 0—Normal; 1—Tail weakness; 2—Hind leg weakness or paralysis; 3—Hind leg paralysis, dragging hind limbs; 4—Complete paralysis, unable to move; 5—Death.

At $28^{th}$ day after EAE induction the animals were sacrificed, blood was collected from rats' hearts. The animals were perfused with 4% PFA, brain and spinal cord were collected and fixed in 4% formaldehyde.

The results are presented at Table 9 below.

TABLE 9

Influence of performed treatment on clinical signs score

| Group | Clinical signs score on day 23 after induction (mean) |
|---|---|
| Group 1 | 1.7 |
| Group 2 | 1.1 |
| Group 3 | 0.5 |
| Group 4 | 0.9 |
| Group 5 | 0.8 |
| Group 6 | 0.3 |
| Group 7 | 0.3 |
| Group 8 | 0.1 |
| Group 9 | 0.9 |

Thus, EAE clinical signs are most efficiently suppressed by oligopeptide GGDRGAPKRGSGKDSHH alone or in combination with oligopeptide GFGYGGRASDYKSAHK and/or oligopeptide QGTLSKIFKLGGRDSRSGSPMARR.

Oligopeptides GFGYGGRASDYKSAHK and oligopeptide QGTLSKIFKLGGRDSRSGSPMARR alone or in combination has moderate therapeutic effect. Combination of oligopeptide GGDRGAPKRGSGKDSHH with oligopeptide GFGYGGRASDYKSAHK and oligopeptide QGTLSKIFKLGGRDSRSGSPMARR has most beneficial therapeutic effect; i.e. oligopeptide QGTLSKIFKLGGRDSRSGSPMARR and/or oligopeptide GFGYGGRASDYKSAHK unexpectedly multiply the positive clinical effect of oligopeptide GGDRGAPKRGSGKDSHH.

The foregoing description of the present invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

We claim:

1. A pharmaceutical composition comprising:
   (a) an oligopeptide that consists of the amino acid sequence GGDRGAPKRGSGKDSHH (SEQ ID NO: 2); and
   (b) (i) an oligopeptide that consists of the amino acid sequence GFGYGGRASDYKSAHK (SEQ ID NO: 3), and/or (ii) an oligopeptide that consists of the amino acid sequence QGTLSKIFKLGGRDSRSGSPMARR (SEQ ID NO: 4).

2. The pharmaceutical composition of claim 1, comprising:
   (a) an oligopeptide that consists of the amino acid sequence GGDRGAPKRGSGKDSHH (SEQ ID NO: 2); and
   (b) (i) an oligopeptide that consists of the amino acid sequence GFGYGGRASDYKSAHK (SEQ ID NO: 3), and (ii) an oligopeptide that consists of the amino acid sequence QGTLSKIFKLGGRDSRSGSPMARR (SEQ ID NO: 4).

3. The pharmaceutical composition of claim 1, wherein one or more oligopeptides are salts.

4. The pharmaceutical composition of claim 1, wherein one or more oligopeptides are acetic acid salts.

5. The pharmaceutical composition of claim 1, wherein the combination of oligopeptides is present in a therapeutically effective amount.

6. The pharmaceutical composition of claim 1, further comprising a pharmaceutically acceptable carrier and/or excipient and/or drug delivery system.

7. The pharmaceutical composition of claim 6, wherein the drug delivery system is liposomes.

8. A method of treating or reducing the incidence of multiple sclerosis in a subject in need of such treatment, wherein said method comprises administering to the subject a therapeutically effective amount of the pharmaceutical composition of claim 1.

9. A method of treating or reducing the incidence of multiple sclerosis in a subject in need of such treatment, wherein said method comprises administering to the subject a therapeutically effective amount of the pharmaceutical composition of claim 2.

* * * * *

SEQUENCE LISTING

```
<160> NUMBER OF SEQ ID NOS: 26

<210> SEQ ID NO 1
<211> LENGTH: 170
<212> TYPE: PRT
<213> ORGANISM: Homo sapiens

<400> SEQUENCE: 1

Ala Ser Gln Lys Arg Pro Ser Gln Arg His Gly Ser Lys Tyr Leu Ala
1               5                   10                  15
```

-continued

```
Thr Ala Ser Thr Met Asp His Ala Arg His Gly Phe Leu Pro Arg His
            20                  25                  30

Arg Asp Thr Gly Ile Leu Asp Ser Ile Gly Arg Phe Phe Gly Gly Asp
        35                  40                  45

Arg Gly Ala Pro Lys Arg Gly Ser Gly Lys Asp Ser His His Pro Ala
50                  55                  60

Arg Thr Ala His Tyr Gly Ser Leu Pro Gln Lys Ser His Gly Arg Thr
65                  70                  75                  80

Gln Asp Glu Asn Pro Val Val His Phe Phe Lys Asn Ile Val Thr Pro
                85                  90                  95

Arg Thr Pro Pro Ser Gln Gly Lys Gly Arg Gly Leu Ser Leu Ser
            100                 105                 110

Arg Phe Ser Trp Gly Ala Glu Gly Gln Arg Pro Gly Phe Gly Tyr Gly
        115                 120                 125

Gly Arg Ala Ser Asp Tyr Lys Ser Ala His Lys Gly Phe Lys Gly Val
    130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Asp Arg Gly Ala Pro Lys Arg Gly Ser Gly Lys Asp Ser His
1               5                   10                  15

His

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Gly Tyr Gly Gly Arg Ala Ser Asp Tyr Lys Ser Ala His Lys
1               5                   10                  15

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gly Thr Leu Ser Lys Ile Phe Lys Leu Gly Gly Arg Asp Ser Arg
1               5                   10                  15

Ser Gly Ser Pro Met Ala Arg Arg
                20
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Gly Ala Pro Val Val His Pro Pro Leu Ala Ile Val Thr Pro Ala
1               5                   10                  15

Thr

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Asn Pro Val Val His Phe Phe Lys Asn Ile Val Thr Pro Arg Thr
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gln Gly Thr Leu Ser Lys Ile Phe Lys Leu Gly Gly Arg Asp
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Glu Asn Pro Val Val His Phe Phe Lys Asn Ile Val Thr Pro Arg
1               5                   10                  15

Thr

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Gly Gly Gly Ser Gly Gly Gly Ser Gly Gly Gly Gly Ser
1               5                   10                  15

<210> SEQ ID NO 10
<211> LENGTH: 26
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 10

Arg Phe Phe Gly Gly Asp Arg Gly Ala Pro Lys Arg Ser Gly Lys
1               5                   10                  15

Asp Ser His His Pro Ala Arg Thr Ala His
            20                  25

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Gly Gly Asp Arg Gly Ala Pro Lys Arg Gly Ser Gly Lys Asp Ser
1               5                   10                  15

His His Pro Ala Arg
            20

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Pro Lys Arg Gly Ser Gly Lys Asp Ser His His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Asp Arg Gly Ala Pro Lys Arg Gly Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Lys Arg Gly Ser Gly Lys Asp Ser His His
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 15

Gly Gly Asp Arg Gly Ala Pro Lys Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Gly Ser Gly Lys Asp Ser His His
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Asp Arg Gly Ala Pro
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Gly Lys Asp Ser His His
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Asp Arg Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Asp Ser His His
1               5

<210> SEQ ID NO 21
<211> LENGTH: 60
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 21

Arg Gly Ala Pro Lys Arg Gly Ser Gly Lys Arg Gly Ala Pro Lys Arg
1               5                   10                  15

Gly Ser Gly Lys Arg Gly Ala Pro Lys Arg Gly Ser Gly Lys Arg Gly
            20                  25                  30

Ala Pro Lys Arg Gly Ser Gly Lys Arg Gly Ala Pro Lys Arg Gly Ser
        35                  40                  45

Gly Lys Arg Gly Ala Pro Lys Arg Gly Ser Gly Lys
    50                  55                  60

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Gly Ala Pro Lys Arg Gly Ser Gly Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Pro Lys Arg Gly Ser Gly Lys Asp Ser His
1               5                   10

<210> SEQ ID NO 24
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Ala Pro Lys Arg Gly Ser Gly Lys Tyr Gly Gly Arg Ala Ser Asp
1               5                   10                  15

Tyr Lys Ser Gly Thr Leu Ser Lys Ile Phe Lys Leu Gly Gly Arg Asp
            20                  25                  30

Ser Arg Arg Gly Ala Pro Lys Arg Gly Ser Gly Lys Tyr Gly Gly Arg
        35                  40                  45

Ala Ser Asp Tyr Lys Ser Gly Thr Leu Ser Lys Ile Phe Lys Leu Gly
    50                  55                  60

Gly Arg Asp Ser Arg
65

<210> SEQ ID NO 25
<211> LENGTH: 57
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 25

Gly Gly Asp Arg Gly Ala Pro Lys Arg Gly Ser Gly Lys Asp Ser His
1               5                   10                  15

His Gly Phe Gly Tyr Gly Gly Arg Ala Ser Asp Tyr Lys Ser Ala His
            20                  25                  30

Lys Gln Gly Thr Leu Ser Lys Ile Phe Lys Leu Gly Gly Arg Asp Ser
        35                  40                  45

Arg Ser Gly Ser Pro Met Ala Arg Arg
    50                  55

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Gly Lys Asp Ser
1               5
```